United States Patent [19]
Knepper, Jr.

[11] Patent Number: 5,377,553
[45] Date of Patent: Jan. 3, 1995

[54] TRANSDUCER SUPPORT DEVICE
[75] Inventor: William H. Knepper, Jr., Katy, Tex.
[73] Assignee: Tuboscope Vetco International, Inc., Houston, Tex.
[21] Appl. No.: 59,590
[22] Filed: May 12, 1993
[51] Int. Cl.⁶ .................................... G01N 27/72
[52] U.S. Cl. ...................................... 73/866.5
[58] Field of Search .............. 73/622, 637, 640, 866.5, 73/151; 324/226, 228, 232, 234–242

[56] References Cited
U.S. PATENT DOCUMENTS

| | | | |
|---|---|---|---|
| 1,933,547 | 11/1933 | Drake et al. | 324/241 |
| 3,185,923 | 5/1965 | Sadofsky | 324/226 |
| 3,955,425 | 5/1976 | Corneau | 73/622 |
| 4,492,115 | 1/1985 | Kahil et al. | |
| 4,555,665 | 11/1985 | Stanley et al. | |
| 4,578,642 | 3/1986 | Moake et al. | |
| 4,611,170 | 9/1986 | Stanley et al. | |
| 4,629,985 | 12/1986 | Papadimitriou et al. | |
| 4,629,991 | 12/1986 | Wheeler | |
| 4,636,727 | 1/1987 | Kahil et al. | |
| 4,698,590 | 10/1987 | Moake et al. | |
| 4,704,580 | 11/1987 | Moake et al. | |
| 4,710,712 | 12/1987 | Bradfield et al. | |
| 4,715,442 | 12/1987 | Kahil et al. | |
| 4,792,756 | 12/1987 | Lam et al. | |
| 4,957,000 | 9/1990 | Delpy et al. | 73/622 |
| 5,030,911 | 7/1991 | Lam | |
| 5,043,663 | 8/1991 | Lam | |

Primary Examiner—Robert Raevis
Attorney, Agent, or Firm—Finnegan, Henderson, Farabow, Garrett & Dunner

[57] ABSTRACT

A transducer support device is provided which when employed with magnet flux leakage detectors renders the detectors sufficiently compact and lightweight to facilitate use thereof at the wellhead to avoid the requirement of a lay-down horizontal inspection at a location apart from the wellhead.

8 Claims, 2 Drawing Sheets

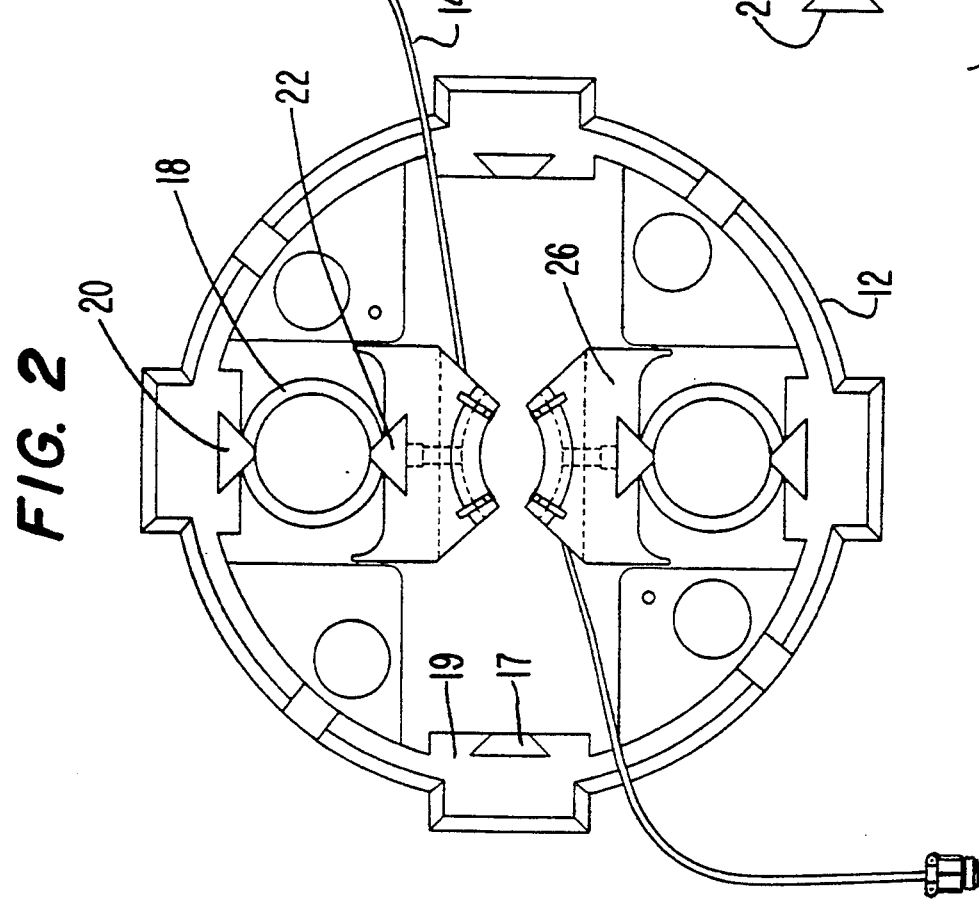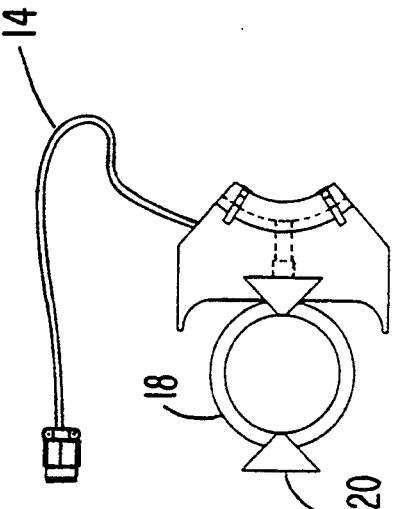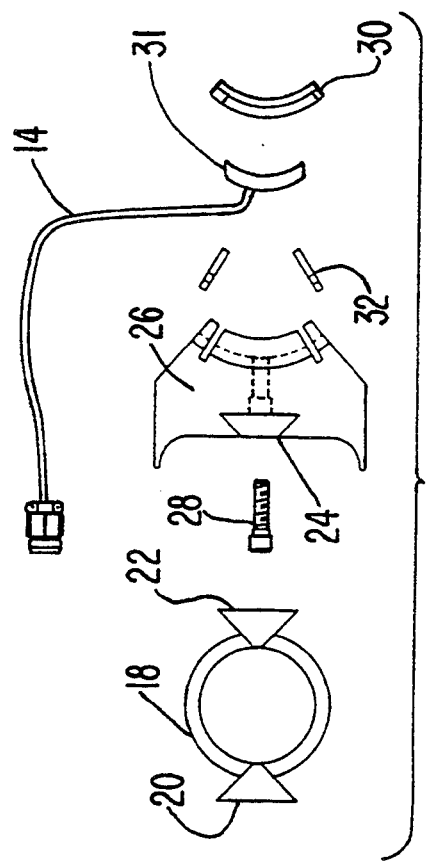

TRANSDUCER SUPPORT DEVICE

BACKGROUND OF THE INVENTION

Field of the Invention

The invention relates to a support device for transducers employed in wellhead scanning devices for inspecting oil and gas pipeline.

Description of the Prior Art

It is necessary in oil and gas extraction operations to assess the integrity of the tubing of the well. This is significant to detect defects before a failure occurs in the well. It is customary practice in oil and gas extraction operations to periodically remove the tubing from the well to permit inspection of the well. During these tubing-removal operations, an excellent opportunity is provided to inspect the tubing for defects without requiring additional down-time of the well.

Common practice for this purpose is to remove the tubing from the well, replace it with a newly-inspected tubing and then perform an inspection of the removed tubing by placing it on horizontal racks to support the same during inspection. This of course is a cumbersome and expensive operation requiring not only substitute tubing but in addition necessitating time-consuming and expensive manipulation and placement of the tubing for inspection at a location apart from the wellhead.

Inspection devices customarily used for this purpose embody flux leakage technology. More specifically, a magnetic coil is used to produce a magnetic flux within the wall of the tubing and in the presence of a defect in the form of a discontinuity, distortion of some of the lines of flux and leakage thereof results. This leakage is detected by employing a series of transducers, which provide an electrical signal to suitable display and/or recording devices which may indicate the presence, location and extent of the defect.

SUMMARY OF THE INVENTION

It is accordingly a primary object of the present invention to provide a transducer support device adapted for use in inspection of tubing for defects at the wellhead.

A more specific object of the invention is to provide a transducer support device that when employed with magnetic flux leakage detectors renders the detectors sufficiently compact and lightweight to facilitate use thereof at the wellhead to avoid the conventional requirement of a lay-down, horizontal inspection at a location apart from the wellhead.

In accordance with the invention, the transducer support device has a frame with an inner surface surrounding an open inner portion of the frame. A plurality of transducers are provided within this open inner portion of the frame, with each transducer being mounted on and connected to the frame by an associated flexible means that permits each transducer to move toward and away from the frame.

The flexible means normally maintains the associated transducer at a position of maximum distance from the inner surface of the frame.

The flexible means permits movement of the associated transducer toward the inner surface of the frame from this position of maximum distance upon application of force to the transducer in a direction toward the inner surface. This force may result from tubing passing through the device in contact with the transducer.

At least one pair of the plurality of transducers are mounted in opposed relation on the flexible means for simultaneously, opposed movement thereof toward and away from the inner surface of the frame upon force application.

The flexible means may include a resilient portion connected on opposite sides to the transducer and the inner surface of the frame. The resilient portion is compressed upon application of force to the transducer toward the inner surface of the frame. This resilient portion is generally ring-shaped.

The transducer is fastened to one side of a connector with an opposite side of the connector having a slot for providing connection to the ring-shaped resilient portion. This may be achieved by embedding the transducer in an arc-shaped holder that is fastened to the one side of the connector.

A magnetizing coil is provided to surround the frame. This magnetizing coil is mounted and adapted to provide a magnetic flux field within the wall of the tubing being inspected, and discontinuities in this flux field indicating defects are detected by the transducers.

BRIEF DESCRIPTION OF THE DRAWINGS

FIG. 2 is a plan view of one embodiment of a transducer support device in accordance with the invention;

FIG. 3 is a detailed view of a portion of the support device of FIG. 2 in assembly; and FIG. 4 is an exploded view of the structure of the support device of FIG. 3.

DETAILED DESCRIPTION OF THE PREFERRED EMBODIMENTS

Figure 1:
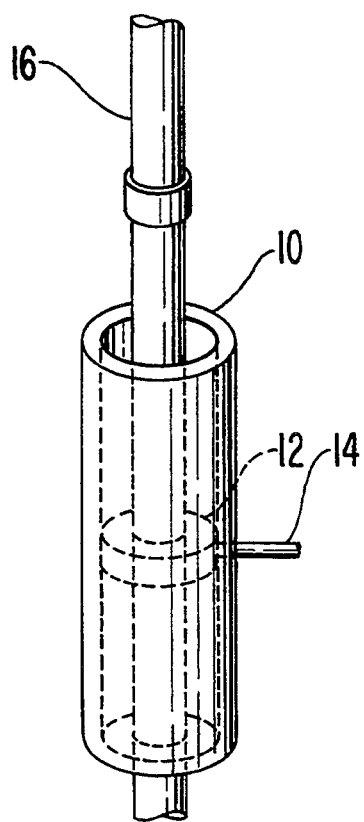
FIG. 1 is a schematic showing of an in-line tubing inspection device having a transducer support device in accordance with the present invention and employing magnetic flux leakage technology.

With reference to the drawings, and for the present to FIG. 1 thereof, there is shown an in-line inspection device for the wellhead inspection of tubing using magnetic flux leakage technology. A magnetizing coil 10 surrounds a ring-shaped support 12 in accordance with embodying pick-up transducers (not shown). The signals from the transducers are provided through conductor 14. A pipeline 16 to be inspected moves upwardly in the direction of the arrow from the wellhead (hot shown) through the support 12. The magnetizing coil 10 provides a magnetic flux field within the walls of the tubing which in the presence of a defect results in flux leakage. Flux leakage is detected by the transducers on the support 12 and a signal indicating a defect is transmitted via conductor 14 to recording and/or displaying equipment (not shown).

As shown ill FIG. 2, the ring-shaped support 12 has on the interior thereof four transducer mountings 19 each having dove-tail slots 17. A ring-shaped flexible member 18, as best shown in FIG. 4, is provided with opposed dove-tail connectors 20 that are secured within slots 17, as shown in FIG. 3. The ring-shaped flexible connector is of urethane or other suitable flexible material. Dove-tail connector 22 is adapted for insertion into dove-tail slot 24 of transducer shoe 26. Transducer shoe 26 is connected by screw 28 to an arc-shaped transducer shoe blank 30 constituting a holder for detecting magnetic flux leakage and providing a signal through conductor 14. Strikers 32 protect the shoe blank 30 from wear and provide a rigid bearing surface for contact with a pipe coupling during an inspection operation to transmit force from contact with the coupling to flex members 18 and thus retract shoe 26 to permit passage thereof over the sampling.

A series of four of the assemblies shown in FIGS. 3 and 4 are provided in opposed relation on the ring 12, as shown in FIG. 2. As the pipeline 16 is passed between the opposed pairs of transducers, the connectors 18 provide the desired flexible mounting so that contact of the transducers with the exterior surface of the tubing 16 is maintained for effective flux leakage detection. The ring assembly at 12, as described above and shown in FIG. 2, is sufficiently compact that the magnetizing coil 10 may be positioned to surround the ring 12. This is facilitated by the connectors 18 being positioned within the ring thus providing space for the surrounding magnetizing coil. This contributes to the overall compactness and light-weight of the device so that it may be used at the wellhead to inspect pipe during withdrawal frown the well without requiring movement of the tubing to a horizontal support rack apart from the wellhead for inspection in accordance with the conventional practice.

What is claimed is:

1. A transducer support device comprising, a frame having an inner surface surrounding an open inner portion of the frame, a plurality of transducers within said open inner portion of said frame with each transducer of said plurality of transducers mounted on and connected to the frame by an associated flexible means for permitting each transducer to move toward and away from a portion of the inner surface of said frame, each said flexible means having a connection to said portion of the inner surface and constituting a ring constructed of flexible material and adapted for compression toward said connection to said portion of the inner surface upon application of force to each said transducer toward said connection.

2. The device of claim 1 wherein said flexible means normally maintains the associated transducer at a position distant from said inner surface of said frame.

3. The device of claim 2 wherein said flexible means permits movement of the associated transducer toward said connection to said portion of the inner surface of the frame from said position upon application of said force to said transducer.

4. The device of claim 3 wherein at least one pair of said plurality of transducers are mounted in opposed relation on said flexible means for simultaneous opposed movement thereof toward and away from said connection to said portion of the inner surface of said frame.

5. The device of claim 4 wherein each said flexible means is connected on opposite sides to said transducer and to said connection to said portion of said inner surface of said frame.

6. The device of claim 5 wherein each of said transducers is fastened to one side of a connector with an opposite side of the connector having a slot for providing connection to said ring.

7. The device of claim 6 wherein a magnetizing coil is provided to surround said frame.

8. The device of claim 6 wherein each of said transducers is embedded in an arc-shaped holder fastened to said one side of said connector.

* * * * *